United States Patent [19]
Iwasaki et al.

[11] Patent Number: 5,872,284
[45] Date of Patent: Feb. 16, 1999

[54] METHOD FOR PURIFYING CRUDE NAPHTHALENEDICARBOXYLIC ACID

[75] Inventors: Hiroshi Iwasaki; Nobuya Hirokane; Masayasu Ishibashi; Satoshi Inoki, all of Kuga-gun, Japan

[73] Assignee: Mitsui Chemicals, Inc., Tokyo, Japan

[21] Appl. No.: 860,622

[22] PCT Filed: Oct. 30, 1996

[86] PCT No.: PCT/JP96/03180

§ 371 Date: Jul. 9, 1997

§ 102(e) Date: Jul. 9, 1997

[87] PCT Pub. No.: WO97/17318

PCT Pub. Date: May 15, 1997

[30] Foreign Application Priority Data

Nov. 10, 1995 [JP] Japan .................................. 6-293101
May 16, 1996 [JP] Japan .................................. 7-121899

[51] Int. Cl.$^6$ .................................................. C07C 51/42
[52] U.S. Cl. ............................................. 562/486; 562/487
[58] Field of Search .................... 562/485, 487; 560/78

[56] References Cited

U.S. PATENT DOCUMENTS 5,256,817  10/1993  Sikkenga et al. .

FOREIGN PATENT DOCUMENTS

WO 94-20447  9/1994  WIPO .
WO 96-19430  6/1996  WIPO .
WO 97-17318  5/1997  WIPO .

Primary Examiner—Samuel Barts
Attorney, Agent, or Firm—Sherman and Shalloway

[57] ABSTRACT

The invention provides a method for purifying a crude naphthalenedicarboxylic acid comprising the steps of mixing a crude naphthalenedicarboxylic acid and a water/alcohol solvent to esterify a part of the naphthalenedicarboxylic acid, thereby dissolving a naphthalenedicarboxylic ester into the solvent, and then contacting the resulting reaction mixture with hydrogen in the presence of a hydrogenation catalyst to hydrogenate impurities which are contained in the crude naphthalenedicarboxylic acid and which are capable of being hydrogenated, thereby dissolving and removing hydrogenation products into the water/alcohol solvent. A mixture of a naphthalene dicarboxylic acid and a naphthalenedicarboxylic ester with reduced impurity contents, or a high-purity naphthalenedicarboxylic acid can be obtained.

14 Claims, No Drawings

METHOD FOR PURIFYING CRUDE NAPHTHALENEDICARBOXYLIC ACID

TECHNICAL FIELD

The present invention relates to a method for purifying a crude naphthalenedicarboxylic acid, which method enables to obtain from a naphthalenedicarboxylic acid containing impurities, a mixture of a naphthalene dicarboxylic acid and a naphthalenedicarboxylic ester with reduced impurity contents, or a high-purity naphthalenedicarboxylic acid.

BACKGROUND ART

A naphthalenedicarboxylic acid can be prepared by, for example, oxidizing a dialkylnaphthalene in the presence of cobalt, manganese and bromine. The crude naphthalenedicarboxylic acid obtained by this process, however, contains impurities, e.g., trimellitic acid and aldehydes, as well as cobalt, manganese and bromine derived from the catalyst. When such a naphthalenedicarboxylic acid is used as a starting material to prepare polyethylene naphthalate, coloring of the resulting polyethylene naphthalate or staining of a mold in the molding process may take place. Therefore, the naphthalenedicarboxylic acid obtained above needs to be purified prior to use.

As a method for purifying a naphthalenedicarboxylic acid, JP-A-1-110650 discloses a process for preparing purified bis(2-hydroxyethyl) 2,6-naphthalenedicarboxylate, which process comprises reacting an impure 2,6-naphthalenedicarboxylic acid with at least 2 mol of ethylene glycol based on 1 mol of the 2,6-naphthalenedicarboxylic acid in the presence of catalytic quantities of a tertiary amine and a titanium-containing compound to prepare bis(2-hydroxyethyl) 2,6-naphthalenedicarboxylate, crystallizing the bis(2-hydroxyethyl) 2,6-naphthalenedicarboxylate, and recovering the purified bis(2-hydroxyethyl) 2,6-naphthalenedicarboxylate.

JP-A-5-508870 discloses a process for preparing a purified dimethyl naphthalenedicarboxylate, which process comprises reacting 2,6-naphthalenedicarboxylic acid with methanol in an appropriate reaction region to prepare a reaction mixture containing dissolved dimethyl 2,6-naphthalenedicarboxylate and monomethyl 2,6-naphthalenedicarboxylate, cooling the reaction mixture to a temperature of not higher than about 40° C. to crystallize main parts of the dissolved dimethyl 2,6-naphthalenedicarboxylate and monomethyl 2,6-naphthalenedicarboxylate, partitionating the crystallized dimethyl 2,6-naphthalenedicarboxylate and monomethyl 2,6-naphthalenedicarboxylate from the reaction mixture mother liquor, heating the partitionated dimethyl 2,6-naphthalenedicarboxylate and monomethyl 2,6-naphthalenedicarboxylate in a recrystallization solvent to a temperature high enough to dissolve at least a part of the dimethyl 2,6-naphthalenedicarboxylate and substantially all of the monomethyl 2,6-naphthalenedicarboxylate, recrystallizing the dimethyl 2,6-naphthalenedicarboxylate dissoloved in the recrystallization solvent at such a temperature that the dimethyl 2,6-naphthalenedicarboxylate is recrystallized while the main parts of the monomethyl 2,6-naphthalenedicarboxylate are retained in the recrystallization mother liquor, and partitionating the recrystallized dimethyl-2,6-naphthalenedicarboxylate from the recrystallization mother liquor.

Further, JP-A-7-173100 discloses a process for preparing a high-purity 2,6-naphthalenedicarboxylic acid, which process comprises dissolving crude crystals of 2,6-naphthalenedicarboxylic acid containing impurities in water in supercritical or subcritical state, cooling the resulting solution at a temperature of not higher than 300° C. to precipitate crystals, and separating the crystals from the mother liquor at a temperature of 100° to 300° C.

In the circumstances, it is desired to develop a method for purifying a naphthalenedicarboxylic acid, wherein impurity contents can be further reduced by easier procedures.

The present invention has been made under such circumstances as described above, and it is an object of the invention to provide a method for purifying a crude naphthalenedicarboxylic acid, which method enables to obtain a mixture of a naphthalenedicarboxylic acid and a naphthalenedicarboxylic ester with reduced impurity contents, or a high-purity naphthalenedicarboxylic acid.

DISCLOSURE OF THE INVENTION

The method for purifying a crude naphthalenedicarboxylic acid according to the present invention comprises the steps of:

mixing a crude naphthalenedicarboxylic acid with a water/alcohol solvent to esterify a part of the naphthalenedicarboxylic acid, thereby dissolving a naphthalenedicarboxylic ester into the solvent, and then contacting the resulting reaction mixture with hydrogen in the presence of a hydrogenation catalyst to hydrogenate impurities which are contained in the crude naphthalenedicarboxylic acid and which are capable of being hydrogenated, thereby dissolving and removing hydrogenation products into the water/alcohol solvent.

In an embodiment of the present invention, the hydrogenation step may be followed by crystallizing the naphthalenedicarboxylic acid and naphthalenedicarboxylic ester to obtain a mixture of the naphthalenedicarboxylic acid and naphthalenedicarboxylic ester with reduced impurity contents.

In another embodiment of the invention, the hydrogenation step may be followed by a further step, wherein the alcohol concentration in the water/alcohol solvent is lowered to hydrolyze the naphthalenedicarboxylic ester, and recovering the resulting naphthalenedicarboxylic acid.

According to the present invention, a high-purity naphthalenedicarboxylic acid can be prepared from a crude naphthalenedicarboxylic acid.

A preferred alcohol used in the present invention is methanol, ethanol or ethylene glycol.

In the present invention, the naphthalenedicarboxylic acid obtained may be washed with water or alcohol.

BEST MODE FOR CARRYING OUT THE INVENTION

According to the present invention, a crude naphthalenedicarboxylic acid is mixed with a water/alcohol solvent to esterify a part of the naphthalenedicarboxylic acid, thereby dissolving an ester produced into the solvent, and then resulting reaction mixture is contacted with hydrogen in the presence of a hydrogenation catalyst to hydrogenate impurities which are contained in the crude naphthalenedicarboxylic acid, thereby dissolving and removing hydrogenation products into the water/alcohol.

The crude naphthalenedicarboxylic acid used in the invention may be one prepared by, for example, oxidizing a dialkylnaphthalene in the presence of cobalt, manganese and bromine. Such a crude naphthalenedicarboxylic acid generally contains impurities capable of being hydrogenated, such as trimellitic acid, aldehydes, 4-formyl-2-naphthoic acid and 6-formyl-2-naphthoic acid, and impurities derived from catalyst, such as cobalt, manganese and bromine.

In the present invention, first, the crude naphthalenedicarboxylic acid as mentioned above is mixed with a water/alcohol solvent to esterify a part of the naphthalenedicarboxylic acid.

The naphthalenedicarboxylic acid may be used in an amount of 0.007 to 0.5 mol, preferably 0.03 to 0.10 mol, based on 1 mol of an alcohol in the water/alcohol solvent. The alcohol concentration in the water/alcohol solvent may be 20 to 95% by weight, preferably 40 to 90% by weight, more preferably 40 to 70% by weight. The alcohol used for the water/alcohol solvent preferably has up to 8 carbon atoms, and examples thereof include aliphatic alcohols, such as methanol, ethanol, propanol, isopropanol, butanol, pentanol, hexanol, heptanol and octanol; alicyclic alcohols, such as cyclohexanol; aromatic alcohols, such as phenol and benzyl alcohol; and dihydric alcohols, such as ethylene glycol. Of these, methanol, ethanol and ethylene glycol are particularly preferable. Mixtures of alcohols can also be used.

The esterification of the naphthalenedicarboxylic acid may be carried out under a pressure of 2 to 80 kg/cm$^2$, preferably 10 to 50 kg/cm$^2$, at a temperature of 200° to 300° C., preferably 160° to 280° C., for 0.2 to 6 hours, preferably 1 to 4 hours. It is preferred to esterify the naphthalenedicarboxylic acid so as to obtain an esterification degree of generally 20 to 90%, preferably 40 to 70%, though it varies depending on the alcohol concentration in the water/alcohol solvent. The esterification degree is a value calculated by the following equation.

$$\text{Esterification degree (\%)} = \frac{\text{Number of carboxyl groups esterified}}{\text{Number of all the carboxyl groups before esterification}} \times 100$$

By the esterification reaction, a naphthalenedicarboxylic monoester and a naphthalenedicarboxylic diester are produced, and these naphthalenedicarboxylic monoester and naphthalenedicarboxylic diester dissolve into the water/alcohol solvent.

Then, in order to remove impurities which are contained in the crude naphthalenedicarboxylic acid and which are capable of being hydrogenated, the reaction mixture obtained from the esterification step is contacted with hydrogen in the presence of a hydrogenation catalyst to hydrogenate the impurities. The resulting hydrogenation products dissolve away into the water/alcohol solvent.

The hydrogenation of the impurities may be carried out under a pressure of 20 to 80 kg/cm$^2$, preferably 30 to 60 kg/cm$^2$, at a temperature of 160° to 300° C., preferably 200° to 280° C., for 0.05 to 2.0 hours, preferably 0.1 to 1.0 hour. Examples of the hydrogenation catalysts employable herein include those conventionally known, such as Fe, Co, Ni, Ru, Rh, Pd, Os, Ir and Pt. The hydrogenation catalyst may be used in an amount of 0.0005 to 1% by weight, preferably 0.003 to 0.3% by weight, in terms of metal in the hydrogenation catalyst, based on the total weight of the naphthalenedicarboxylic acid, alcohol and water.

By virtue of the hydrogenation, the impurities capable of being hydrogenated are converted into compounds soluble in the water/alcohol solvent.

Through the above step, the impurities, which are contained in the crude naphthalenedicarboxylic acid and which are capable of being hydrogenated, can be removed.

In the present invention, the hydrogenation step may be followed by cooling the resulting solution to crystallize the naphthalenedicarboxylic acid and the naphthalenedicarboxylic esters. Thus, separation of crystallized product from the water/alcohol solvent provides a mixture of the naphthalenedicarboxylic acid and the naphthalenedicarboxylic esters containing reduced amounts of impurities.

The ratio between the naphthalenedicarboxylic acid and the naphthalenedicarboxylic esters can be adjusted by controlling the alcohol concentration in the water/alcohol solvent and/or the temperature for the crystallization.

To obtain a high-purity naphthalenedicarboxylic acid according to the present invention, the alcohol concentration in the water/alcohol solution containing the naphthalenedicarboxylic acid and the naphthalenedicarboxylic esters obtained from the hydrogenation of the impurities, can be lowered to hydrolyze the naphthalenedicarboxylic esters. The resulting naphthalenedicarboxylic acid precipitates and can be recovered by separation.

The alcohol concentration may be lowered in any suitable manners including, but not limited thereto, for example, adding water to the water/alcohol solution, evaporating a part of the alcohol from the water/alcohol solution, or adding to the water/alcohol solution a water/alcohol solvent having a lower alcohol concentration. Before the alcohol concentration in the solution is lowered as mentioned above, a part of the solvent may be removed from the water/alcohol solution obtained by the hydrogenation of the impurities.

In the hydrolysis process, the alcohol concentration in the water/alcohol solvent may not be higher than 60% by weight, preferably not higher than 40% by weight, more preferably not higher than 30% by weight.

The hydrolysis may be carried out under a pressure of 2 to 80 kg/cm$^2$, preferably 10 to 50 kg/cm$^2$, at a temperature of 160° to 300° C., preferably 200° to 280° C., for 0.2 to 6 hours, preferably 1 to 4 hours.

After the hydrolysis, the naphthalenedicarboxylic acid can be crystallized by cooling the water/alcohol solution. The crystallized naphthalenedicarboxylic acid is separated from the water/alcohol solvent to obtain a high-purity naphthalenedicarboxylic acid.

If the naphthalenedicarboxylic acid obtained above is washed with an alcohol such as methanol and ethanol, or water, or a mixture of these solvents, a naphthalenedicarboxylic acid of much higher purity can be obtained.

The high-purity naphthalenedicarboxylic acid obtained by the method according to the invention can suitably be used as a starting material for preparing polyethylene naphthalate.

EFFECT OF THE INVENTION

According to the present invention, a mixture of a naphthalenedicarboxylic acid and a naphthalenedicarboxylic ester with reduced impurity contents, or a high-purity naphthalenedicarboxylic acid can be obtained using easy procedures.

EXAMPLE

The present invention will be further described with reference to the following examples, but it should be construed that the invention is not limited to those examples.

Example 1

A crude 2,6-naphthalenedicarboxylic acid (NDA) containing impurities shown in Table 1 was subjected to the following steps (1), (2) and (3) to purify the crude NDA.

(1) Esterification step 120 g of methanol and 80 g of water (methanol concentration in the solvent system: 60% by weight) were added to 40 g of NDA and the mixture was charged in a 500 ml autoclave. The reaction system was purged with nitrogen (pressure: 10 kg/cm$^2$) and heated at 250° C. for 4 hours, followed by cooling the autoclave. Through this process, most of the NDA was esterified to produce a mixture containing NDA monoester and NDA diester. The resulting mixture (I) had a composition set forth in Table 1.

(2) Hydrogenation step

Subsequently, 2 g of 0.5% Pd/C particles were placed in a Ti wire mesh catalyst cage which was set in the autoclave so as to allow it to move up and down therein. Then, the system was purged with hydrogen (pressure: 10 kg/cm$^2$) and heated again. When the internal temperature of the autoclave reached 250° C., the catalyst cage was lowered into the solution to contact the catalyst with the solution. After 20 minutes, the catalyst cage was lifted to separate from the solution, followed by cooling the autoclave.

(3) Hydrolysis step

Thereafter, the catalyst cage was taken away from the autoclave. To the hydrogenation reaction product were added 4 g of methanol and 136 g of water so that the methanol concentration in the solvent became 20% by weight. The resulting mixture was fed to the autoclave again, which was then purged with nitrogen (pressure: 10 kg/cm$^2$) and heated at 250° C. for 4 hours. Thereafter, the autoclave was cooled to 25° C. to precipitate crystals which were separated. Thus, 41 g of the crystals were recovered The impurity contents and composition of the recovered. crystals (II) are set forth in Table 1.

Example 2

The whole amount (41 g) of the crystals recovered after the hydrolysis step (3) of Example 1 was washed first with 500 g of methanol at 70° C. and then with 500 g of hot water at 70° C. to obtain 34 g of washed crystals (III). The analyzed values of the washed crystals (III) are set forth in Table 1.

TABLE 1

|  |  | Ex. 1 |  | Ex. 2 |
| --- | --- | --- | --- | --- |
|  |  | (I) | (II) | (III) |
| Impurity | Co | 50 | not | 2 | <1 |
| content | Mn | 380 | analyzed | 10 | <1 |
| (ppm) | TMLA | 48 |  | <1 | <1 |
|  | FNA | 2,940 |  | 35 | 35 |
| Composition | NDA | 100 | 9 | 88 | 99 |
| (%) | NDA-mMe | 0 | 50 | 9 | 1 |
|  | NDA-dMe | 0 | 41 | 3 | 0 |

(I): analyzed values of the mixture (I) obtained by the esterification step
(II): analyzed values of the crystals (II) recovered after the hydrogenation step and the hydrolysis step
(III): analyzed values of the purified crystals (III)
TMLA: trimellitic acid
FNA: 6-formyl-2-naphthoic acid
NDA-mMe: monomethyl ester of naphthalenedicarboxylic acid
NDA-dMe: dimethyl ester of naphthalenedicarboxylic acid Examples 3–6

A crude naphthalenedicarboxylic acid was purified in the same manner as in Example 1 except that a water/alcohol solvent shown in Table 2 was used in place of the water/methanol solvent. The amounts of impurities contained in the resulting NDA (purified NDA) are set forth in Table 2.

TABLE 2

| Solvent |  | Ex. 3 water/EtOH | Ex. 4 water/EG | Ex. 5 water/IPA | Ex. 6 water/PhOH |
| --- | --- | --- | --- | --- | --- |
| Impurity | Co | <1 | <1 | <1 | <1 |
| content | Mn | <1 | <1 | <1 | <1 |
| (ppm) | TMLA | 58 | <1 | 30 | 22 |
|  | FNA | 73 | 90 | 85 | 120 |

EtOH: ethanol
EG: ethylene glycol
IPA: isopropanol
PhOH: phenol

Example 7

(1) A 1,000 ml autoclave was charged with 100 g of a crude 2,6-naphthalenedicarboxylic acid containing impurities shown in Table 3, 240 g of methanol and 160 g of water. A Ti wire mesh catalyst cage filled with a hydrogenation catalyst (0.5% Pd/C particles, 8 g) was set in the autoclave so as to be movable up and down therein. The system was purged with hydrogen and pressurized with hydrogen to 3 kg/cm$^2$ and then with nitrogen to 10 kg/cm$^2$.

(2) The system was heated at 245° C. for 4 hours to esterify NDA. Then, the catalyst cage was lowered into the solution to contact the catalyst with the solution, and hydrogenation reaction was performed at the same temperature for 10 minutes.

(3) Hydrolysis

Subsequently, the internal pressure of the autoclave was slowly lowered, and 250 g of water was added over a period of 3 hours to hydrolyze the esterification product of NDA, while 220 g of the methanol was distilled off from the top of a distillation column equipped on the autoclave.

(4) Washing with hot water

Thereafter, the autoclave was cooled to 150° C. and the resulting crystals of NDA were separated from the liquid by withdrawing it into a receiver. Then, 400 g of water heated to 150° C. was fed to the autoclave and the mixture was stirred for 20 minutes to wash the NDA. The NDA was separated from the liquid again, and the liquid was withdrawn into a receiver. After addition of 400 g of water, the autoclave was cooled to 25° C. The resulting crystals were separated from the liquid. Thus, 95 g of the crystals (purified NDA) were recovered. The impurity contents and the compositions of the resulting purified NDA and the starting crude NDA are set forth in Table 3.

TABLE 3

|  |  | Crude NDA | Purified NDA |
| --- | --- | --- | --- |
| Impurity | Co | — | — |
| content | Mn | — | — |
| (ppm) | TMLA | 140 | <1 |
|  | FNA | 5,100 | 33 |
| Composition | NDA | 100 | 99.9 |
| (%) | NDA-mMe | 0 | 0.1 |
|  | NDA-dMe | 0 | 0 |

—: not analyzed

Example 8

(1) A 1,000 ml autoclave was charged with 100 g of a crude 2,6-naphthalenedicarboxylic acid containing impurities shown in Table 4, 240 g of ethylene glycol and 160 g of water. A Ti wire mesh catalyst cage filled with a hydrogenation catalyst (0.5% Pd/C particles, 8 g) was set in the autoclave so as to be movable up and down therein. The system was purged with hydrogen and pressurized with hydrogen to 3 kg/cm² and then with nitrogen to 10 kg/cm².

(2) The system was heated at 245° C. for 2 hours to esterify NDA. Then, the catalyst cage was lowered into the solution to contact the catalyst with the solution for 10 minutes to perform the hydrogenation reaction.

(3) Thereafter, the autoclave was cooled to 25° C. and the pressure was lowered to atmospheric pressure. The resulting crystals and the liquid were taken out as a slurry from the autoclave, to which 1,000 ml of water was added. The crystals were separated from the liquid. Thus, 120 g of the crystals (purified NDA-EG ester mixture) were recovered. The impurity contents and the composition of the purified NDA-EG ester mixture are set forth in Table 4.

TABLE 4

|  |  | Crude NDA | Purified NDA |
|---|---|---|---|
| Impurity | Co | 140 | — |
| content | Mn | 676 | — |
| (ppm) | TMLA | 130 | <1 |
|  | FNA | 5,590 | 30 |
| Composition | NDA | 100 | 23 |
| (%) | NDA-mEG | 0 | 47 |
|  | NDA-dEG | 0 | 25 |
|  | Oligomer | 0 | 5 |

—: not analyzed
MDA-mEG: 2-carboxyl-6-hydroxyethoxycarbonylnaphthalene
MDA-dEG: 2,6-bis(hydroxyethoxycarbonyl)naphthalene
Oligomer: oligomer of NDA-diethylene glycol Example 9

The operation of Example 7 was repeated several times to prepare 206 g of purified NDA.

A glass flask equipped with a distillation apparatus was charged with 206 g of the NDA obtained above and 186 g of EG. The flask was then immersed in an oil bath at 80° C. and heated to 225° C. over a period of 30 minutes, followed by keeping the same temperature. The water produced in this process was distilled and recovered from the top of the distillation column. When water produced in esterification was no longer distilled, esterification reaction was regarded as completed.

To the esterification product of NDA obtained above were added 21 mg of germanium dioxide as a polymerization catalyst and a solution obtained by dissolving 15 mg of tetraethylammonium hydroxide and 39 mg of phosphoric acid in 5 g of EG as a stabilizer. The mixture of the esterification product, the polymerization catalyst and the stabilizer was heated to 260° C. and stirred for 1 hour while recovering the distilled EG. Then, the pressure of the reaction system was reduced to not higher than 1 Torr, and the system was heated to 280° C. over 1 hour to further distill EG. The reaction was further continued for 1.5 hours at 280° C. under a reduced pressure of not higher than 1 Torr with distilling EG to obtain a polyethylene naphthalate.

The polyethylene naphthalate had an intrinsic viscosity (measured in o-chlorophenol/phenol (1/1) at 25° C.) of 0.55 dl/g, a glass transition temperature (Tg, measured by a differential scanning calorimeter) of 111° C. and a melting temperature (Tm) of 266° C.

What is claimed is:

1. A method for purifying a crude naphthalenedicarboxylic acid, which method comprises the steps of:

mixing a crude naphthalenedicarboxylic acid with a water/alcohol solvent to esterify a part of the naphthalenedicarboxylic acid, thereby dissolving a naphthalenedicarboxylic ester into the solvent, and then contacting the resulting reaction mixture with hydrogen in the presence of a hydrogenation catalyst to hydrogenate impurities which are contained in the crude naphthalenedicarboxylic acid and which are capable of being hydrogenated, thereby dissolving and removing hydrogenation products into the water/alcohol solvent.

2. A method for purifying a crude naphthalenedicarboxylic acid, comprising the steps of:

mixing a crude naphthalenedicarboxylic acid and a water/alcohol solvent to esterify a part of the naphthalenedicarboxylic acid, thereby dissolving a naphthalenedicarboxylic ester into the solvent, then contacting the resulting reaction mixture with hydrogen in the presence of a hydrogenation catalyst to hydrogenate impurities which are contained in the crude naphthalenedicarboxylic acid and which are capable of being hydrogenated, thereby dissolving and removing hydrogenation products into the water/alcohol solvent, and crystallizing the naphthalenedicarboxylic acid and naphthalenedicarboxylic ester.

3. A method for purifying a crude naphthalenedicarboxylic acid, comprising the steps of:

mixing a crude naphthalenedicarboxylic acid and a water/alcohol solvent to esterify a part of the naphthalenedicarboxylic acid, thereby dissolving a naphthalenedicarboxylic ester into the solvent, then contacting the resulting reaction mixture with hydrogen in the presence of a hydrogenation catalyst to hydrogenate impurities which are contained in the crude naphthalenedicarboxylic acid and which are capable of being hydrogenated, thereby dissolving and removing hydrogenation products into the water/alcohol solvent, and lowering the alcohol concentration in the water/alcohol solvent to hydrolyze the naphthalenedicarboxylic ester, and recovering the resulting naphthalenedicarboxylic acid.

4. The method for purifying a crude naphthalenedicarboxylic acid as claimed in any one of claims 1 to 3, wherein the alcohol concentration in the water/alcohol solvent during the esterification of a part of the naphthalenedicarboxylic acid is 40 to 70% by weight.

5. The method for purifying a crude naphthalenedicarboxylic acid as claimed in claim 4, wherein the alcohol concentration in the water/alcohol solvent during the hydrolysis of the naphthalenedicarboxylic ester is not higher than 30% by weight.

6. The method for purifying a crude naphthalenedicarboxylic acid as claimed in any one of claims 1 to 3, wherein the alcohol is methanol, ethanol or ethylene glycol.

7. The method for purifying a crude naphthalenedicarboxylic acid as claimed in any one of claims 1 to 3, further comprising washing the naphthalenedicarboxylic acid obtained with water or alcohol.

8. The method for purifying a crude naphthalenedicarboxylic acid as claimed in claim 4, wherein the alcohol is methanol, ethanol or ethylene glycol.

9. The method for purifying a crude naphthalenedicarboxylic acid as claimed in claim 5, wherein the alcohol is methanol, ethanol or ethylene glycol.

10. The method for purifying a crude naphthalenedicarboxylic acid as claimed in claim 4, further comprising washing the naphtalenedicarboxylic acid obtained with water or alcohol.

11. The method for purifying a purifying a crude naphthalenedicarboxylic acid as claimed in claim 5, further comprising washing the naphthalenedicarboxylic acid obtained with water or alcohol.

12. The method for purifying a crude naphthalenedicarboxylic acid as claimed in claim 6, further comprising washing the naphthalenedicarboxylic acid obtained with water or alcohol.

13. The method for purifying a crude naphthalenedicarboxylic acid as claimed in claim 8, further comprising washing the naphthalenedicarboxylic acid obtained with water or alcohol.

14. The method for purifying a crude naphthalenedicarboxylic acid as claimed in claim 9, further comprising washing the naphthalenedicarboxylic acid obtained with water or alcohol.

* * * * *